US011067490B2

United States Patent
Jiang et al.

(10) Patent No.: US 11,067,490 B2
(45) Date of Patent: Jul. 20, 2021

(54) BRACKET, SUPPORT SYSTEM, AND THROMBELASTOGRAPHY DEVICE AND USE METHOD THEREOF (71) Applicant: NEOTEK BIOSCIENCE CO., LTD., Jiangsu (CN)

(72) Inventors: Feng Jiang, Jiangsu (CN); Jian Xiao, Jiangsu (CN); Gong Liu, Jiangsu (CN); Aiqin Chen, Jiangsu (CN); Bangzhong Yu, Jiangsu (CN)

(73) Assignee: NEOTEK BIOSCIENCE CO., LTD., Jiangsu (CN)

( * ) Notice: Subject to any disclaimer, the term of this patent is extended or adjusted under 35 U.S.C. 154(b) by 0 days.

(21) Appl. No.: 16/097,016

(22) PCT Filed: May 2, 2017

(86) PCT No.: PCT/CN2017/082786
§ 371 (c)(1),
(2) Date: Oct. 26, 2018

(87) PCT Pub. No.: WO2017/186190
PCT Pub. Date: Nov. 2, 2017

(65) Prior Publication Data
US 2019/0137377 A1 May 9, 2019

(30) Foreign Application Priority Data

Apr. 29, 2016 (CN) .......................... 201610278393.1
Apr. 29, 2016 (CN) .......................... 201610279824.6
(Continued)

(51) Int. Cl.
*G01N 11/14* (2006.01)
(52) U.S. Cl.
CPC ........ *G01N 11/14* (2013.01); *G01N 2011/147* (2013.01)

(58) Field of Classification Search
CPC ...... G01N 11/10; G01N 11/14; G01N 11/142; G01N 11/16; G01N 11/162; G01N 11/167; G01N 2011/145; G01N 2011/147
(Continued)

(56) References Cited

U.S. PATENT DOCUMENTS 4,328,701 A    5/1982  Mau-Tung et al.
4,736,624 A *  4/1988  Arnstein ................. G01N 11/14
                                                                73/54.35
(Continued)

FOREIGN PATENT DOCUMENTS

CA        1223458 A  *  6/1987  ............. G01N 11/14
CN      104062207 A     9/2014
(Continued)

OTHER PUBLICATIONS

International Search Report issued for International Patent Application No. PCT/CN2017/082786, dated Jul. 24, 2017, 8 pages including English translation.
(Continued)

*Primary Examiner* — Nathaniel J Kolb
(74) *Attorney, Agent, or Firm* — Hamre, Schumann, Mueller & Larson, P.C.

(57) ABSTRACT

A bracket, a support system, and a thrombelastography device and use method thereof are disclosed. The bracket comprises: a first support part (1001), a second support part (1003), and a connection part (1002), wherein the first support part (1001) supports the second support part (1003) by means of the connection part (1002), so that the second support part (1003) can rotate relative to the first support part (1001) under a first action force. The first support part (1001) comprises: a rotatable structure (1004), a support base (1013), and a stop mechanism (1024), wherein the stop mechanism (1024) is used for applying a stop force to the
(Continued)

rotation of the rotatable structure (1004), the rotatable structure (1004) is supported on the support base (1013) and can rotate relative to the support base (1013) under a second action force when the stop force of the stop mechanism (1024) is eliminated, and the rotatable structure (1004) supports the second support part (1003) by means of the connection part (1002), so that the rotatable structure (1004) can rotate relative to the second support part (1003) while rotating relative to the support base (1013). Angular shifts of test parts of the thrombelastography device can be adjusted, thereby improving the measurement accuracy.

18 Claims, 7 Drawing Sheets

(30) Foreign Application Priority Data

Apr. 29, 2016 (CN) .......................... 201620380387.2
Apr. 29, 2016 (CN) .......................... 201620383166.0

(58) Field of Classification Search
USPC .................... 73/54.28–54.34, 64.41–64.43
See application file for complete search history.

(56) References Cited

U.S. PATENT DOCUMENTS

| | | | |
|---|---|---|---|
| 5,201,214 A * | 4/1993 | Sekiguchi | G01N 11/14 |
| | | | 73/54.33 |
| 5,301,541 A * | 4/1994 | Joseph | G01N 11/14 |
| | | | 73/54.28 |
| 6,225,126 B1 | 5/2001 | Cohen et al. | |
| 2010/0154520 A1 | 6/2010 | Schubert et al. | |
| 2016/0091516 A1 | 3/2016 | Gorin et al. | |

FOREIGN PATENT DOCUMENTS

| | | |
|---|---|---|
| CN | 104181311 A | 12/2014 |
| CN | 104458503 | 3/2015 |
| CN | 104614539 A | 5/2015 |
| JP | 2002537560 | 11/2002 |
| JP | 2012515340 | 7/2012 |
| WO | 2010081876 | 7/2010 |

OTHER PUBLICATIONS

Office Action issued for Japanese Patent Application No. 2019-507986, Dispatch Date: Feb. 16, 2021, 6 pages including English machine translation.

\* cited by examiner

BRACKET, SUPPORT SYSTEM, AND THROMBELASTOGRAPHY DEVICE AND USE METHOD THEREOF

TECHNICAL FIELD

The present invention relates to the technical field of measurement, in particular, to a bracket, a support system, and a thrombelastography device and use method thereof.

BACKGROUND

A thrombelastography device is an apparatus which is configured to measure blood coagulation parameters of blood in vitro and comprises a rotary shaft that is rotatable. When blood is measured, the rotary shaft is inserted into the blood and rotates as the blood rotates. The elasticity of the blood is calculated according to the angular displacement of the rotary shaft within a set measurement time, thereby providing objective guidance for clinical diagnosis of diseases such as cardiovascular and cerebrovascular diseases.

At present, the rotary shaft on the thrombelastography device is connected to a bracket. Under the support of the bracket, the rotary shaft rotates under a driving force of the blood.

SUMMARY

Embodiments of the present invention provide a bracket, a support system, and a thrombelastography device and a use method thereof, which can adjust an angular offset conveniently, thereby improving the measurement accuracy.

According to an aspect of the present invention, there is provided a bracket, which comprises a first support part, a second support part, and a connection part, wherein the first support part supports the second support part by means of the connection part, so that the second support part can rotate relative to the first support part under a first action force;

the first support part comprises: a rotatable structure, a support base, and a stop mechanism, wherein the stop mechanism is used for applying a stop force to the rotation of the rotatable structure;

the rotatable structure is supported on the support base and can rotate relative to the support base under a second action force when the stop force of the stop mechanism is eliminated; and the rotatable structure supports the second support part by means of the connection part, so that the rotatable structure can rotate relative to the second support part while rotating relative to the support base.

According to another aspect of the present invention, there is provided a thrombelastography device, which comprises the bracket as described above and a rotary shaft, wherein the lower end of the second support part and one end of the rotary shaft are connected to support the rotary shaft, such that the rotary shaft can rotate under an external driving force.

According to yet another aspect of the present invention, there is provided a support system, which comprises the bracket as described above, and a supported object, wherein the lower end of the second support part and one end of the supported object are connected to support the supported object, such that the supported object can rotate under an external driving force.

According to a further aspect of the present invention, there is provided a use method for the thrombelastography device as described above, comprising:

eliminating a stop force of the stop mechanism in response to the first support part being offset from the second support part by a predetermined position;

rotating the first support member by applying the second action force to the first support member, such that the bridge structure rotates relative to the second support part to a position that forms a predetermined angle with the second support part;

inserting the lower end of the rotary shaft to measured blood;

rotating the measured blood to drive the rotary shaft to rotate; and calculating blood coagulation data of the measured blood based on the measured rotation angle of the rotary shaft.

According to respective embodiments of the bracket, the support system, and the thrombelastography device and use method thereof, the first support part and the second support part can rotate relative to each other by means of the connection part, which connects the first support part and the second support part, of the bracket, and the bridge structure, which bears the connection part, of the first support part is located on the rotatable first support member, such that the first support part rotates by applying an appropriate external force to the first support member when the stop force of the stop mechanism to the rotation of the rotatable structure is eliminated, thereby driving the bridge structure to rotate relative to the second support part. Therefore, the bridge structure can be conveniently adjusted to a predetermined angle with the second support part to eliminate angular offset between various parts (e.g., the first support part and the second support part) of the thrombelastography device, thereby improving the measurement accuracy.

The above summary is only for an illustrative purpose and is not intended to be limited in any way. Except for the aspects, embodiments and features as described above, further aspects, embodiments, and features of the present invention will be readily apparent from the appended drawings and the following detailed description.

BRIEF DESCRIPTION OF THE DRAWINGS

In order to illustrate the embodiments of the present invention or the technical solutions in the prior art more clearly, the drawings used in the embodiments or the prior art description will be briefly described below. Apparently, the drawings in the following description are some embodiments of the present invention. For those of ordinary skill in the art, other drawings may also be obtained according to these drawings, without paying creative work. In the drawings, unless otherwise specified, the same reference numerals used throughout the drawings refer to the same or similar components and elements. The drawings are not necessarily to scale. It is should be understood that these drawings are merely illustrative of some embodiments of the present invention and are not to be construed as limiting the scope of the present invention.

DETAILED DESCRIPTION

In order to make the objective, the technical solution and the advantages of the embodiments of the present invention clearer, the technical solutions in the embodiments of the present invention are clearly and completely described below with reference to the accompanying drawings in the embodiments of the present invention. It is apparent that the described embodiments are part of the embodiments of the present invention, rather than all of the embodiments. All other embodiments obtained by those of ordinary skill in the art based on the embodiments of the present invention without paying creative work should fall within the protection scope of the present invention.

In the following, only certain exemplary embodiments are briefly described. As those skilled in the art will recognize, the described embodiments may be modified in various different ways, without departing from the spirit or scope of the present invention. Therefore, the drawings and description are to be regarded as exemplary, rather than restrictive.

In the description of the present invention, it should be understood that, the terms "center", "longitudinal", "transverse", "length", "up", "down", "front", "rear", "left", "right", "vertical", "horizontal", "top", "bottom", "inner", "outer", "clockwise", "counterclockwise" and the like, which denote orientations or positional relationship, are based on the orientations or positional relationships shown in the drawings, for the purposes of describing the present invention and simplifying the description, do not indicate or imply that the device or component referred to necessarily has a specific orientation or is constructed and operated according to a specific orientation, and are therefore not to be construed as limiting the present invention. Moreover, the terms "first" and "second" are used for descriptive purposes only and are not to be construed as indicating or implying a relative importance or implicitly indicating the number of technical features indicated. Thus, features defining "first" or "second" may include one or more of the described features, either explicitly or implicitly. In the description of the present invention, the meaning of "a plurality of" is two or more, unless specifically defined otherwise.

Figure 1:
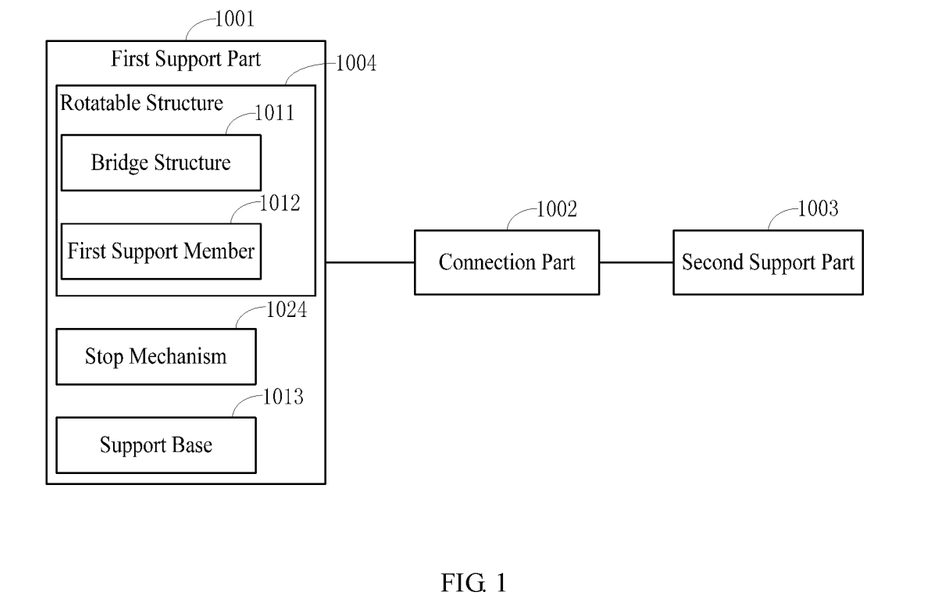
FIG. 1 is a schematic block diagram of a bracket according to an embodiment of the present invention.

As shown in FIG. 1, an embodiment of the present invention provides a bracket, which comprises a first support part 1001, a second support part 1003, and a connection part 1002, wherein the first support part 1001 supports the second support part 1003 by means of the connection part 1002, so that the second support part 1003 can rotate relative to the first support part 1001 under a first action force;

the first support part 1001 comprises: a rotatable structure 1004, a support base 1013, and a stop mechanism 1024, wherein the stop mechanism 1024 is used for stopping the rotation of the rotatable structure 4;

the rotatable structure 1004 is supported on the support base 1013 and can rotate relative to the support base 1013 under a second action force when the stop force of the stop mechanism 1024 to the rotation is eliminated, and the rotatable structure 1004 supports the second support part 1003 by means of the connection part 1002, so that the rotatable structure 1004 can rotate relative to the second support part 1003 while rotating relative to the support base 1013.

In an example as shown in FIG. 1, the rotatable structure 1004 comprises a first support member 1012 and a bridge structure 1011, wherein the first support member 1012 is supported on the support base 1013 and can rotate relative to the support base 1013 under the second action force when the stop force of the stop mechanism 1024 to the rotation is eliminated;

the bridge structure 1011 is supported on the first support member 1012 and fixedly connected to the first support member 1012, such that the bridge structure 1011 can rotate when the first support member 1012 rotates; and the bridge structure 1011 supports the second support part 1003 by means of the connection part 1002, such that the bridge structure 1011 can rotate relative to the second support part 1003 when the first support member 1012 rotates.

The rotatable structure consisting of the first support member and the bridge structure is just an example. It may be understood that the rotatable structure may have other structures.

The stop mechanism 1024 may be implemented in various ways. For example, the stop mechanism 1024 may be selected from one of the followings or any combination thereof:

(1) a fixing member, such as a screw, a latch structure, a rope, or the like for fixing the rotatable structure 1004 relative to the support base 1013. The fixing member may be released when needed to eliminate the step force to the rotation of the rotatable structure 1004.

(2) Surfaces, which are in contact with each other and have predetermined roughness, of the rotatable structure 1004 and the support base 1003. The stop force to the rotation of the rotatable structure 1004 can be provided by an appropriate frictional force between the contact surfaces of the rotatable structure 1004 and the support base 1013. The predetermined roughness may provide a frictional force between the contact surfaces to provide the stop force. For example, the contact surfaces of the rotatable structure and the support base may be machined to have a certain roughness, thereby providing an appropriate frictional force. "The surfaces having a predetermined roughness" used herein includes a material or structure that is connected, adhered, or machined to the contact surfaces for providing or increasing the frictional force. This frictional force can be counteracted by applying an opposing external force when needed, thereby eliminating the stop force to the rotation of the rotatable structure 1004.

(3) A material, which provides an eliminable viscous force, is provided between the contact surfaces of the rotatable structure 1004 and the support base 1013. For example, a reusable viscous material or adhesive material may be provided between the contact surfaces of the rotatable structure 1004 and the support base 1013. The viscous force provided by these materials can be counteracted under an external force. The viscous force continues to stop the rotation of the rotatable structure 1004 as the external force disappears.

Here are just a few examples of the stop mechanism 1024, but are not exhaustive. Other various implementation ways that can implement the functions of the stop mechanism 1024 described herein can be envisioned by those skilled in the art.

Various embodiments of a bracket according to the present invention are described in detail below in conjunction with FIGS. 2-4.

Figure 2A:
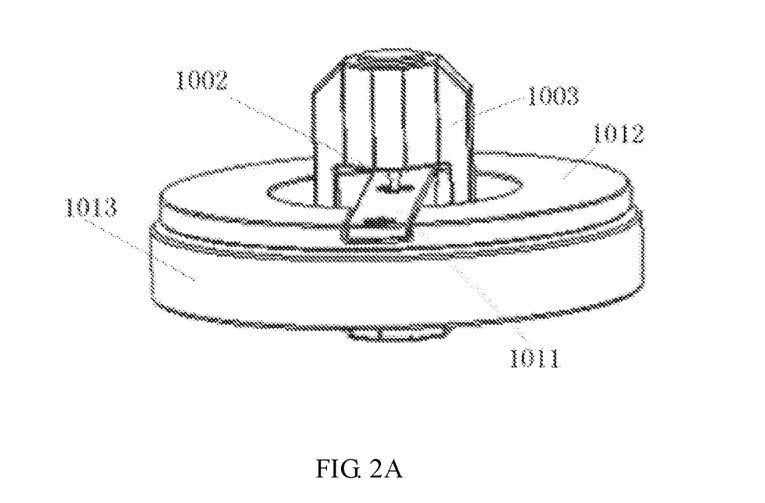
FIGS. 2A-B are structural schematic diagrams of a bracket according to an embodiment of the present invention.
Figure 2B:
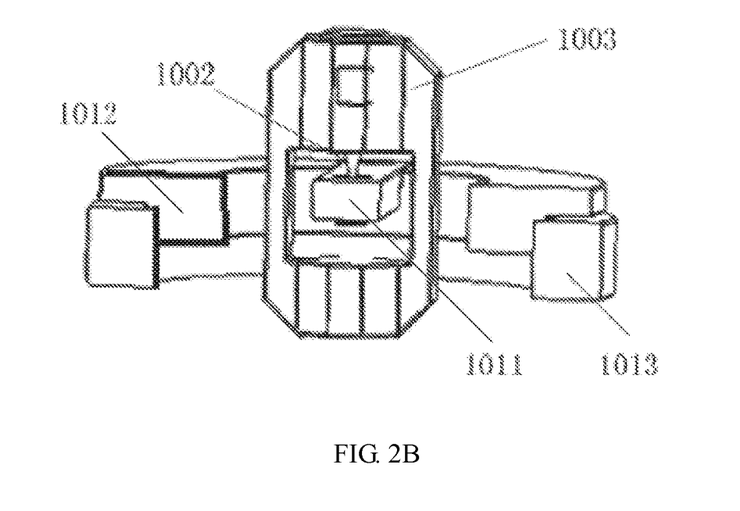

FIG. 2A is a schematic diagram showing the structural composition of a bracket according to an embodiment, and FIG. 2B is a sectional view of FIG. 2A. FIGS. 3A-3C are schematic diagrams showing the composition of a first support part of the bracket in FIG. 2, wherein FIG. 3A is a schematic diagram of the support base, FIG. 3B is a schematic diagram of the first support member, and FIG. 3C is a schematic diagram of the bridge structure. FIG. 4 is a schematic diagram showing the composition of a second support part of the bracket in FIG. 2.

Figure 3A:
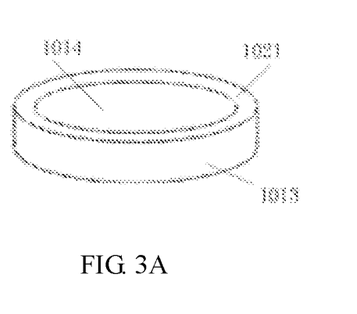
FIGS. 3A-C are schematic diagrams of structural composition of a first support part of the bracket according to an embodiment of the present invention.
Figure 3B:
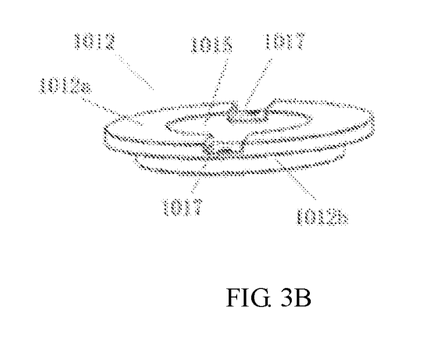
Figures 3C, 4:
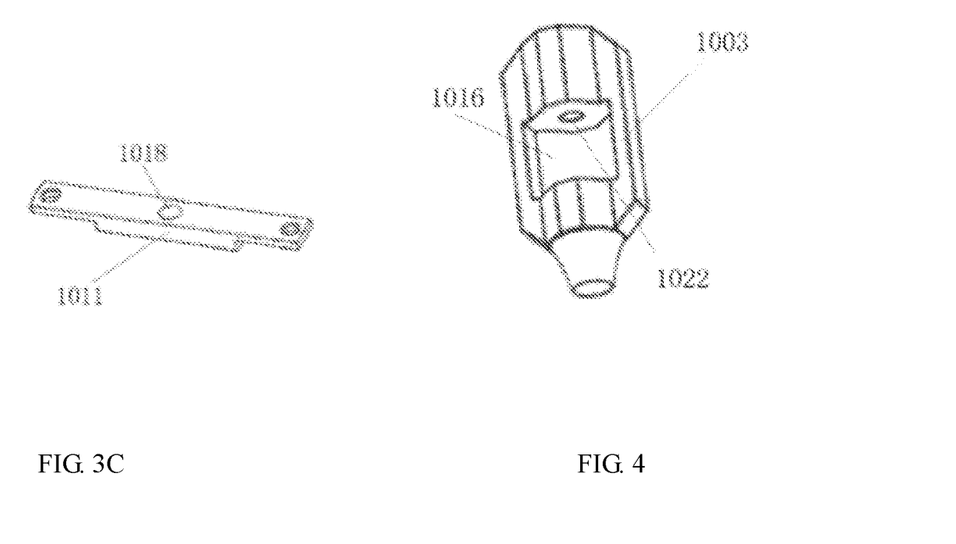
FIG. 4 is a schematic diagram of structural composition of a second support part of the bracket according to an embodiment of the present invention.

In the embodiment of FIGS. 2-4, the bracket is composed of a first support part and a second support part 1003 that are connected by means of a connection part 1002. The first support part comprises a support base 1013, a first support member 1012 which is located on the support base and rotatably connected to the support base, and a bridge structure 1013 supported by the first support member 1012. The first support part is connected to the connection part 1002 by means of the bridge structure 1013 to support the second support part 1003 that is also connected to the connection part 1002. The connection part 1002 is configured such that the second support part 1003 can rotate relative to the first support part under a first action force (for example, when the bracket is applied to a thrombelastography device, the first action force may be a force applied to the second support part 1003 by the rotation of the rotary shaft caused by the rotation of measured blood, wherein the rotary shaft is fixedly connected to the second support part 1003). Therefore, when the supported object that is fixedly connected to the lower end of the second support part 1003 is driven by an external force to rotate, the second support part 1003 can be driven to rotate.

It should be noted that the stop mechanism 1024 in FIG. 1 is not explicitly shown in FIGS. 2-4 for clarity of the graphics. It will be understood that the stop mechanism 1024 can be any of the above mentioned implementations in the examples of FIGS. 2-4.

In the example of FIG. 3, the first support member 1012 comprises a support surface 1012a and a cylindrical extension part 1012b which is located under and connected to the support surface 1012a, wherein the dimension of the top surface of the cylindrical extension part 1012b is smaller than the dimension of the support surface 1012a. That is, the support surface 1012a extends beyond the upper surface of the cylindrical extension part 1012b, such that the support surface 1012a protrudes out of the side surface of the cylindrical extension part 1012b. In this example, the center of the first support member 1012 has a first through hole 1015, and the bridge structure 1011 is fixed to the first support member 1012 across the first through hole 1015.

The bridge structure 1011 may be fixed to the first support member 1012 by a variety of ways with or without the aid of various connection members. For example, the support surface 1012a of the first support member 1012 may be provided with at least one clamping groove in which at least one end of the bridge structure 1011 may be placed. The bridge structure 1011 may be fixed to the first support member 1012 by screws. Or, the bridge structure may be fixed by means of a combination of the two manners. The bridge structure 1011 may also be fixed by welding, bonding, or by means of other connection members and/or fixing members.

In the example as shown in FIGS. 2-4, the support surface 1012a of the first support member 1012 is provided with two clamping grooves 1017 in which two ends of the bridge structure 1011 are placed respectively. For the purpose of further fixation, in this example, two ends of the bridge structure 1011 are also fixed to the first support member 1012 by screws.

In the above example, the bridge structure 1011 is shown as a sunken bridge structure. The upper surface of the bridge structure 1011 is substantially flush with the support surface 1012a of the first support member 1012, a sunken part is arranged under the upper surface, and the upper surface is provided with an orifice 1018 which extends to the sunken part and is used for fixedly connecting the connection part 1002. Those skilled in the art will recognize that the bridge structure 1011 may also be of other structures, such as a floating structure, wherein the lower surface of the bridge structure 1011 is substantially flush with the support surface 1012a of the first support member 1012, a floating part is arranged over the lower surface, and the upper surface is provided with an orifice that extends to the floating part and used for fixedly connecting the connection part 1002.

As shown in FIG. 3A, in this example, the support base 1013 is provided with a top surface 1021. The top surface 1021 is provided with a groove or a second through hole 1014 which is matched with the cylindrical extension part 1012b of the first support member 1012, such that the cylindrical extension part 1012b can be accommodated in the groove or the second through hole 1014. The first support member 1012 may be rotatably connected to the support base 1013 by means of a plurality of connection ways, e.g., a rotating bearing or a sliding bearing. In the example shown in FIGS. 2-4, after being assembled, the first support member 1012 is in direct contact with the support base 1013. The cylindrical extension part 1012 b of the first support member 1012 is accommodated in the second through hole 1014 in the center of the support base 1013. The support surface 1012a of the first support member 1012 is supported on the top surface 1021 of the support base 1013. After the stop force of the stop mechanism to the rotation of the first support member 1012 is eliminated, the first support member 1012 may rotate relative to the support base 1013 when an appropriate external force for rotating the first support member 1012 is applied to the first support member 1012.

In the example of FIGS. 2-4, the support surface 1012a of the first support member 1012 is illustrated to extend beyond the upper surface of the cylindrical extension part 1012b, so as to be in contact with and supported by the top surface 1021 of the support base 1013 after being assembled with the support base 1013. However, it can be understood that the first support member 1012 can also take other forms. For example, the size of the support surface 1012a may be equal to the size of the upper surface of the cylindrical extension part 1012b. After the support surface and the support base 10133 are assembled, the bottom surface of the groove or second through hole 1014 contacts the bottom surface of the cylindrical extension part 1012b and provides support for the bottom surface of the cylindrical extension part. In this way, the first support member is cylindrical, and the groove or through hole of the support base has at least a part of the bottom surface to provide support for the first support member.

In the above examples, the support surface 1012a of the first support member 1012 is circular, the cylindrical extension part 1012b is cylindrical, and the support base 1013 is also cylindrical. Those skilled in the art will understand that the support surface 1012a of the first support member 1012 may be in any shape, and the cylindrical extension part 1012b and the support base 1013 may be in other appropriate shapes, as long as the first support member 1012 may be rotatably connected to the support base 1013.

In the example shown in FIGS. 2-4, the center of each of the support base 1013 and the first support member 1012 is provided with a through hole, and the first through hole 1015 is at least partially overlapped with the second through hole 1014, such that the second support part 1003 at least partially passes through the first through hole 1015 and the second through hole 1014 (see FIGS. 2A-B). It may be understood that the support base 1013 and the first support member 1012 may not be provided with through holes either in the case that it is unnecessary for the second support part 1003 to pass through the first support part 1001.

In the example as shown in FIG. 4, the center of the second support part 1003 is also provided with a through hole, i.e., the third through hole 1016. The side wall, close to the upper end of the second support part 1003, of the third through hole 1016 is provided with a recess 1022 which is connected to the connection part 1002. The third through hole 1016 is illustrated as a square shape in FIG. 4, and it may be understood that it may be in any other appropriate shape.

As can be seen from the schematic diagrams 2A and 2B of the assembled bracket, the second support part 1003 passes through the first through hole 1015 of the first support member 1012 and the second through hole 1014 of the support base 1013 when supported by the first support part 1001, wherein the lower end of the second support part 1003 passes through the support base 1013. In addition, the bridge structure 1011 passes through the third through hole 1016 of the second support part 1003 to support the second support part 1003 by means of the connection part 1002. The orifice 1018 in the bridge structure 1011 is aligned with the recess 1022 in the second support part 1003 and is respectively connected to the connection part 1002. In the assembled bracket, the connection part 1002 is located in the third through hole 1016 of the second support part 1003.

The above bracket structure and assembly method are just of an example. It can be understood that the second support part may also not pass through the first and second through holes, but the second support part and the third through hole thereof are made to be large enough such that the entire first support part can pass through the third through hole, that is, the four frames of the third through hole are all located outside the first support part.

Figure 5:
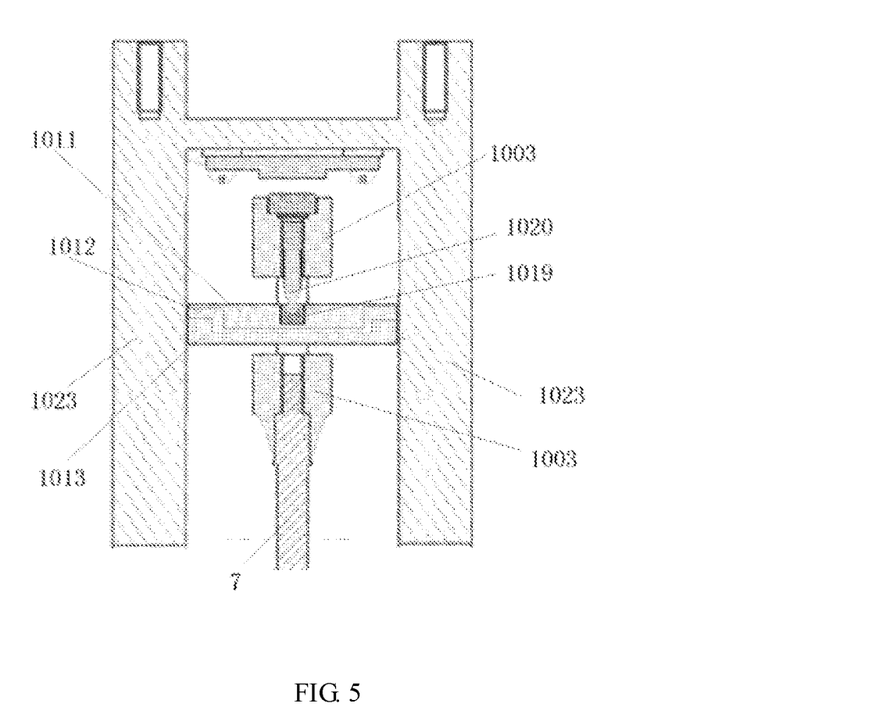
FIG. 5 is a schematic diagram of structural composition of a thrombelastography device according to an embodiment of the present invention.

As can be seen from the example of FIG. 5, the connection part 1002 may comprise a first connection part 1019 and a second connection part 1020, wherein the first connection part 1019 is fixedly connected to the bridge structure 1011 (e.g., by means of the orifice 1018 in the bridge structure 1011). The second connection part 1020 is fixedly connected to the second support part 1003 (e.g., by means of the recess 1022 in the second support part 1003). The first connection part 1019 and the second connection part 1020 are connected together in a form of point contact, such that the first connection part 1019 can rotate relative to the second connection part 1020, and further the second support part 1003 can rotate relative to the bridge structure 1011.

In the example shown in FIG. 5, the first support part supports the second support part and the supported object by means of the connection part, the first connection part 1019 and the second connection part 1020 in the connection part are connected together in a form of point contact, and the supported object is fixedly connected to the second support part and drives, under an external force, the second support part 1003 to rotate around the contact point between the first connection part 1019 and the second connection part 1020. Since the first connection part 1019 and the second connection part 1020 are connected together in a form of point contact, when the first support part 1001 rotates relative to the second support part 1003, only one contact point generates a frictional force to impede the rotation of the second support part 1003. Therefore, the frictional force generated on the bracket may be reduced, and the rotational resistance encountered when the supported object rotates is reduced.

In an embodiment provided by the present invention, the point connection may be in a manner that two contact components are not in full contact and the contact area is less than a predetermined value. For example, when the first connection part 1019 and the second connection part 1020 are connected together in a form of point contact, the contact area is less than 1 square millimeter.

Figure 6:
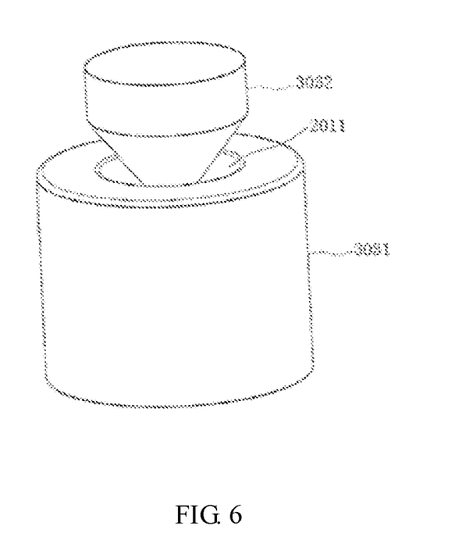
FIG. 6 is a schematic diagram of composition of a connection part according to an embodiment of the present invention.

FIG. 6 illustrates a schematic diagram of a connection part in which the first connection part and the second connection part are a jewel bearing 3031 and a top cone 3032. The jewel bearing 3031 is provided with a tapered groove 2011; the top cone 3032 may be of a tapered structure, and the tip of the top cone 3032 is located in the tapered groove 2011 in the jewel bearing 3031; the top cone 3032 is engaged with the jewel bearing 3031 in a form of point contact.

As shown in FIG. 6, the jewel bearing 3031 is of a cake structure. The tapered groove 2011 is formed in a plane of the jewel bearing 3031. The top cone 3032 may be of a tapered structure. The tip of the top cone 3032 is located in the groove 2011, and only the tip of the top cone 3032 is in contact with the bottom of the groove 2011, such that the jewel bearing 3031 is connected to the top cone 3032 in a form of point contact. For example, when the tip of the top cone 3032 has an area of 0.8 square millimeter, the top cone is in point contact with the tapered groove 2011 of the jewel bearing 3031 by means of this tip having the area of 0.8 square millimeter.

In an embodiment of the present invention, the first connection part of the connection part is a jewel bearing, and the second connection part is a top cone. In another embodiment, the first connection part is a top cone and the second connection part is a jewel bearing.

Figure 7:
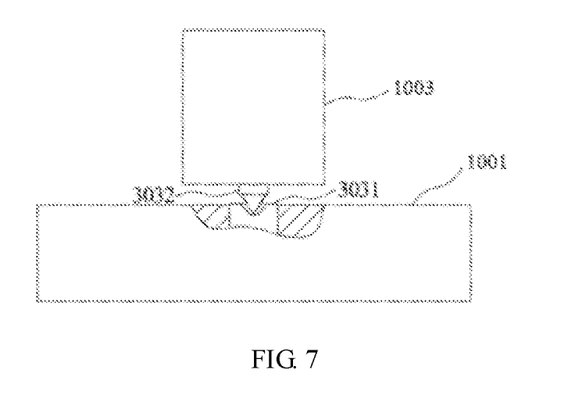
FIG. 7 is a schematic diagram of a connection part for fixedly connecting a jewel bearing to a first support part according to an embodiment of the present invention.

In an example shown in FIG. 7, the jewel bearing 3031 which serves as the first connection part is fixedly connected to the first support part 1001, the top cone 3032 which serves as the second connection part is fixedly connected to the second support part 1003, and the tip of the top cone 3032 is located in a groove of the jewel bearing 3031 and is in point contact with the bottom of the groove of the jewel bearing 3031. The first support part 1001 supports, by means of the jewel bearing 3031, the top cone 3032 and the second support part 1003 which are fixedly connected.

Figure 8:
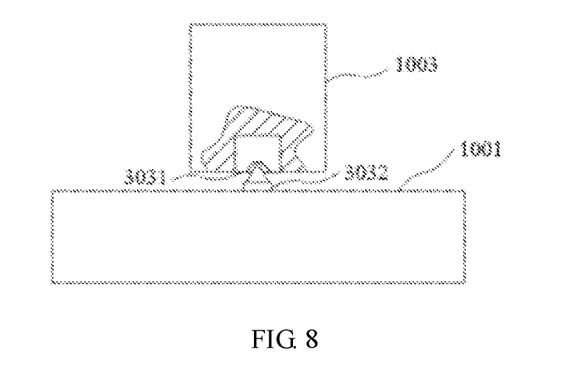
FIG. 8 is a schematic diagram of a connection part for fixedly connecting a jewel bearing to a second support part according to an embodiment of the present invention.

In an embodiment shown in FIG. 8, the top cone 3032 which serves as the first connection part is fixedly connected to the first support part 1001, the jewel bearing 3031 which serves as the second connection part is fixedly connected to the second support part 1003, and the tip of the top cone 3032 is in point contact with the bottom of the jewel bearing 3031. The first support part 1001 supports, by means of the top cone 3032, the jewel bearing 3031 and the second support part 1003 which are fixedly connected.

In an embodiment of the present invention, the bracket further comprises at least a pair of magnets;

for each pair of magnets, the first magnet is fixed to one side, close to the second support part, on the first support part, and the second magnet is fixed to one side, close to the first support part, on the second support part; and the first magnet and the second magnet are stacked in parallel, and two surfaces that are close each other are like magnetic poles.

Figure 9:
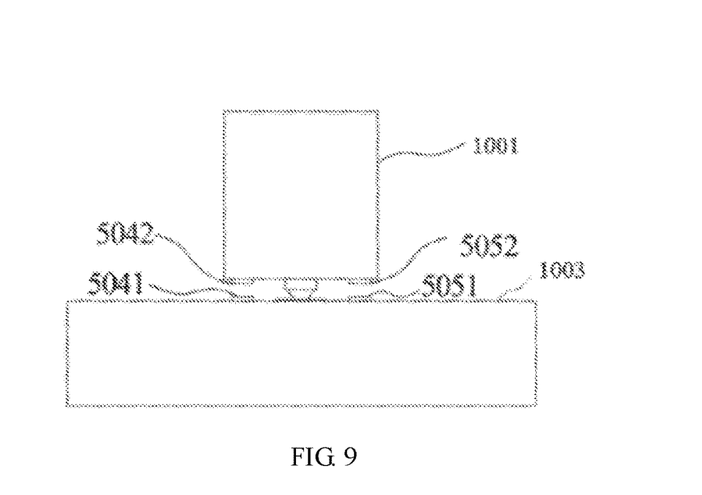
FIG. 9 is a schematic diagram of a connection part comprising magnets according to an embodiment of the present invention.

In an example shown in FIG. 9, the bracket comprises two pairs of magnets. The first pair of magnets includes a magnet 5041 and a magnet 5042. The second pair of magnets includes a magnet 5051 and a magnet 5052. The magnet 5041 and the magnet 5051 are fixed to the first support part 1001, and the magnet 5042 and the magnet 5052 are fixed to the second support part 1003. The magnet 5041 and the magnet 5042 in the first pair of magnets are stacked in parallel. The surfaces, which are close to each other, of the magnet 5041 and the magnet 5042 have magnetic poles which have the same polarity, for example, the N pole of the magnet 5041 is directed to the second support part 1003, and the N pole of the magnet 5042 is directed to the first support part 1001; the magnet 5051 and the magnet 5052 in the second pair of magnets are stacked in parallel; the surfaces, which are close to each other, of the magnet 5051 and the magnet 5052 have magnetic poles which have the same polarity, for example, the S pole of the magnet 5051 is directed to the second support part 1003, and the S pole of the magnet 5052 is directed to the first support part 1001.

In an example shown in FIG. 5, the bracket further comprises a fixed column 1023 for supporting the first support part 1001 and the second support part 1003, wherein the support base 1013 is fixedly connected to the fixed column 1023.

In various embodiments of the bracket described above, the second support part can rotate relative to the first support part (e.g., the bridge structure of the first support part) under a first action force applied thereto, such that the supported object may rotate to drive the second support part to rotate relative to the first support part the lower end of the second support part is connected to the supported object. The first support part kept stationary when the stop force of the stop mechanism to the rotation of the rotatable structure is not eliminated. Therefore, the rotation angle of the supported object may be measured by measuring the rotation angle of the second support part. When necessary (for example, when it is necessary to adjust the angular relationship between the first support part and the second support part to improve the measurement accuracy), the stop force of the stop mechanism to the rotation can be eliminated (for example, by loosening a fixing member, offsetting the frictional force and/or viscous force, or the like). Then, the rotatable structure can rotate relative to the second support part under a second action force applied thereto, such that the first support part (for example, the bridge structure) and the second support part can be placed in a predetermined positional relationship by manually rotating the rotatable structure (for example, the first support member) to ensure the measurement accuracy. Generally, for convenience of measurement, the first support part and the second support part need to be arranged such that the axis of the bridge structure in a length direction is perpendicular to the plane of the second support part. When it is found that the bridge structure of the first support part and the second support part deviate from the predetermined positional relationship, it is necessary to adjust them to the predetermined relationship so as to ensure the measurement accuracy. In this case, by means of the bracket including the rotatable bridge structure according to the present invention, it is possible to apply an appropriate external force to the first support member after the stop force of the stop mechanism to the rotation is eliminated, such that the first support member and the bridge structure fixedly connected thereto rotate by a certain angle relative to the second support part, and therefore the axis of the bridge structure on the bracket becomes perpendicular to the second support part.

The term "bridge structure" as used herein refers to a structure which strides across a surface supporting it. It should be noted that the surface supporting the bridge structure may be provided with slots, openings or through holes for the bridge structure to stride across, but these slots, openings, through holes or the like are not necessary.

Various embodiments of the bracket described herein can be applied to a thrombelastography device. FIG. 5 illustrates an embodiment of the thrombelastography device comprising the bracket described above. As shown in FIG. 5, the thrombelastography device comprises the bracket and a rotary shaft which serves as the supported object supported by the bracket. The lower end of the second support part 1003 is connected to one end of the rotary shaft 7 to support the rotary shaft 7, so that the rotary shaft 7 can rotate under an external driving force. In use, the other end (lower end) of the rotary shaft 7 extends into measured blood in a container, and the blood is driven to rotate by a drive device, thereby driving the rotary shaft 7 to rotate as well. The blood coagulation parameter data of the measured blood may be calculated by the thrombelastography device through measuring the rotation angle of the rotary shaft 7.

In an embodiment of the present invention, the thrombelastography device further comprises a measurement device which is used for measuring a rotation angle of the rotary shaft, and forming a thrombelastogram corresponding to the measured blood according to the rotation angle of the rotary shaft.

Figure 10:
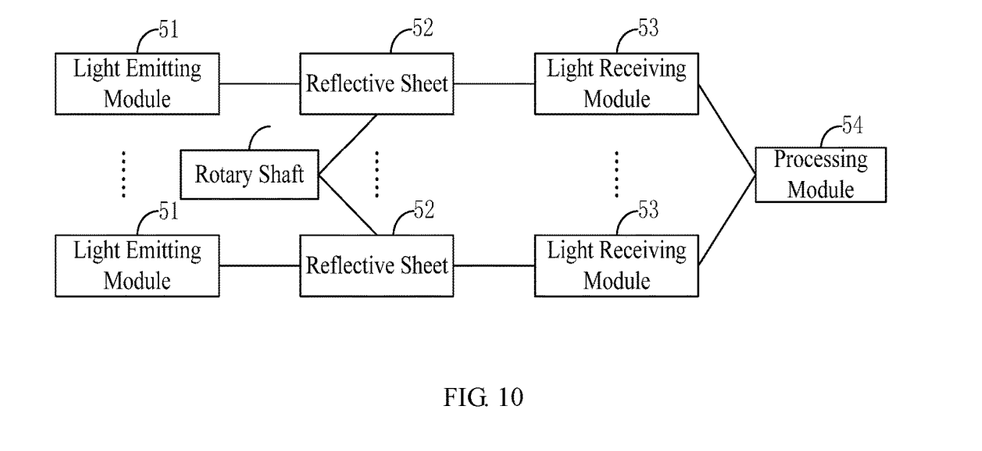
FIG. 10 is a schematic diagram of composition of the thrombelastography device comprising a measurement device according to an embodiment of the present invention.

In an example shown FIG. 10, the measurement device comprises at least one reflective sheet 51, at least one light emitting module 52, at least one light receiving module 53 and a processing module 54, wherein the rotary shaft 7 is fixedly connected to the at least one reflective sheet 51 and drives the at least one reflective sheet 51 to rotate under an external driving force;

each of the light emitting modules 52 is used for emitting light to the corresponding reflective sheet 51 in a fixed direction;

each of the reflective sheets 51 is used for receiving light emitted by the corresponding light emitting module 52 and reflecting the received light;

each of the light receiving modules 53 is used for receiving light reflected by the corresponding reflective sheet 51 in a fixed direction, converting the received light into a corresponding electrical signal according to the intensity of the light, and transmitting the electrical signal to the processing module 54; and the processing module 54 is used for processing the electrical signal converted by the at least one light receiving module 53 to determine the rotation angle of the rotary shaft 7.

According to the thrombelastography device provided by this embodiment, the reflective sheet reflects the light emitted by the light emitting module to the light receiving module. When the reflective sheet rotates under the driving of the rotary shaft, since the light emitting module emits light in a fixed direction, the amount of light received by the reflective sheet changes, and at the same time, the optical path of light reflected by the reflective sheet changes due to the rotation of the reflective sheet, resulting in a change in the intensity of light received by the light receiving module that receives the light in the fixed direction. The light receiving module converts the received light into a corresponding electrical signal according to the intensity of the light. The processing module determines the rotation angle of the rotary shaft according to the electrical signal. In this case, the light is taken as a signal for detecting the rotation angle of the rotary shaft. Since the intensity of the light does not change as external factors such as temperature change, the accuracy of detecting the rotation angle of the rotary shaft can be improved by detecting the rotation angle of the rotary shaft through light.

Figure 11:
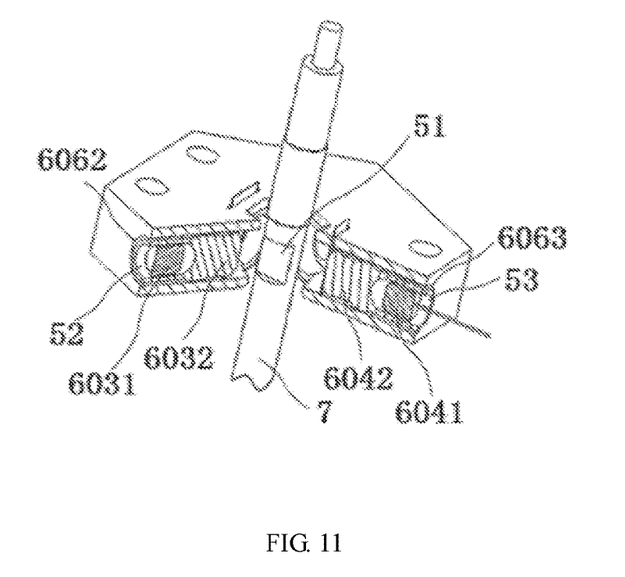
FIG. 11 is a schematic diagram of composition of the thrombelastography device comprising a light emitting diode and a photocell according to an embodiment of the present invention.

In an example shown in FIG. 11, the light emitting module 52 comprises a light emitting diode 6031 and a light guide column 6032, wherein the light emitting diode 6031 emits light to the reflective sheet 51 through the light guide column 6032;

and/or the light receiving module 53 comprises a photocell 6041 and a light guide column 6042, wherein the photocell 6041 receives light reflected by the reflective sheet 51 through the light guide column 6042.

In the embodiment of the present invention, since the inner surface of a fourth through hole 6062 where the light emitting module 52 is located is a machined surface which has a certain roughness, if the light emitting diode 6031 directly emits light to the reflective sheet 51, the light emitted by the light emitting diode 6031 will be diffusely reflected within the fourth through hole 6062, resulting in loss of light energy on the one hand, and difficulty in control over the direction and amount of light outgoing from the fourth through hole 6062 on the other hand. The light emitted from the light emitting diode 6031 is directed to the reflective sheet 51 through the light guide column 6032. The light emitted from the light emitting diode 6031 is conducted inside the light guide column 6032, and may not be diffusely reflected, thereby increasing the utilization rate of the light energy and ensuring that the light emitted from the fourth through hole 6062 has a specific direction and a specific amount, and further ensuring the accuracy of detecting the rotation angle of the rotary shaft 7.

In an embodiment of the present invention, each of the light receiving modules comprises a photocell and a light guide column which are fixed in a fifth through hole respectively, wherein the light guide column is located close to the reflective sheet. The light guide column receives the light reflected by the corresponding reflective sheet in a fixed direction, and transmits the received light to the photocell. The photocell converts the received light into a corresponding electrical signal according to the intensity of the light.

In an example shown in FIG. 11, since the fifth through hole 6063 is formed by machining, the inner surface of the fifth through hole 6063 has a certain roughness. If the light reflected by the reflective sheet 51 directly enters the fifth through hole 6063 and reaches the photocell 6041, the light will be diffusely reflected on the inner wall of the fifth through hole 6063, resulting in the loss of light energy. The energy of the light finally reaching the photocell 6041 is less than the energy of the light entering the fifth through hole 6063, resulting in a relatively large error in the finally detected rotation angle of the rotary shaft 7. The light reflected by the reflective sheet 51 is received by the light guide column 6042, and the light is transmitted inside the light guide column 6042 and is not diffusely reflected during the transmission, thereby ensuring that the energy of the light received by the photocell 6041 is equal to the energy of light reflected by the reflective sheet 51 to the light guide column 6042, and further ensuring the accuracy of detecting the rotation angle of the rotary shaft 7.

In an embodiment of the present invention, the thrombelastography device further comprises at least one light blocking sheet, the number of the light blocking sheets being equal to the number of the light guide columns, and each of the light blocking sheets corresponding to one light guide column. Each light blocking sheet is provided with a light passing hole having a fixed shape and a fixed size. The light blocking sheet is arranged between the reflective sheet and the light guide column, so that the light reflected by the reflective sheet can only be emitted to the light guide column through the light passing hole in the light blocking sheet.

Figure 12:
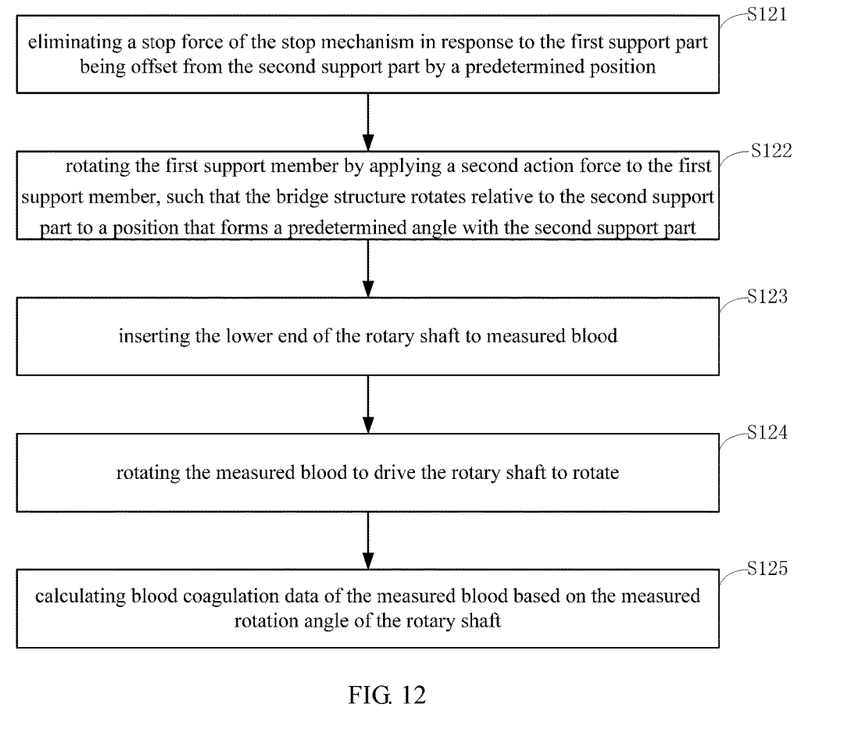
FIG. 12 is a flowchart of a use method for a thrombelastography device according to an embodiment of the present invention.

FIG. 12 illustrates a flowchart of a use method for the thrombelastography device according to an embodiment of the present invention. As shown in FIG. 12, the method comprises:

Step S121: eliminating a stop force of the stop mechanism in response to the first support part being offset from the second support part by a predetermined position;

Step S122: rotating the first support member by applying a second action force to the first support member, such that the bridge structure rotates relative to the second support part to a position that forms a predetermined angle with the second support part;

Step S123: inserting the lower end of the rotary shaft to measured blood;

Step S124: rotating the measured blood to drive the rotary shaft to rotate; and Step S125: calculating blood coagulation data of the measured blood based on the measured rotation angle of the rotary shaft.

Figure 13:
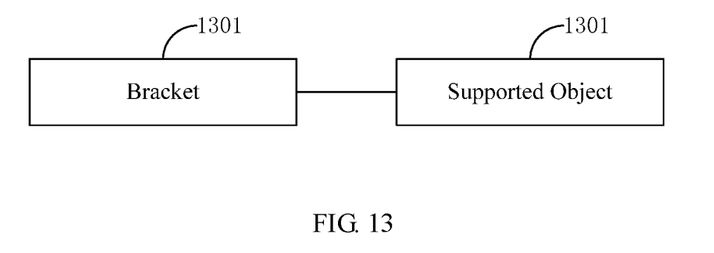
FIG. 13 is a schematic block diagram of a support system according to an embodiment of the present invention.

Although the above description has been made by using the bracket for the thrombelastography device as an example, it can be appreciated that the bracket of various embodiments of the present invention may also be used for other supported objects to form a support system. FIG. 13 illustrates a compositional block diagram of such a support system. As shown FIG. 13, the support system comprises a bracket 1301 and a supported object 1302, wherein the lower end of a second support part of the bracket 1301 and one end of the supported object 1302 are connected to support the supported object 1302, such that the supported object 1302 can rotate under an external driving force.

Various embodiments provided by the present invention have the following beneficial effects:

1. in the embodiment of the present invention, the second support part can rotate relative to the first support part under the first action force applied thereto, such that the supported object can rotate to drive the second support part to rotate relative to the first support part when the lower end of the second support part is connected to the supported object. The first support part kept stationary when the stop force of the stop mechanism to the rotation of the rotatable structure is not eliminated. Therefore, the rotation angle of the supported object may be measured by measuring the rotation angle of the second support part. When necessary (for example, when it is necessary to adjust the angular relationship between the first support part and the second support part to improve the measurement accuracy), the stop force of the stop mechanism to the rotation can be eliminated (for example, by loosening a fixing member, offsetting the frictional force and/or viscous force, or the like). Then, the rotatable structure can rotate relative to the second support part under the second action force applied thereto, such that the first support part (for example, the bridge structure) and the second support part can be placed in a predetermined positional relationship by manually rotating the rotatable structure (for example, the first support member) to ensure the measurement accuracy.

2. In the embodiment of the present invention, the first support part supports the second support part and the supported object by means of the connection part. The first connection part and the second connection part in the connection part are connected together in a form of point contact. The supported object which is in stress drives the second support part to rotate around the contact point between the first connection part and the second connection part. Since the first connection part and the second connection part are connected together in a form of point contact, when the second support part and the first support part rotate relative to each other, only one contact point generates a frictional force to impede the rotation of the second support part. Therefore, the frictional force generated on the bracket may be reduced, and thus the rotational resistance encountered when the supported object rotates is reduced.

3. In the embodiment of the present invention, two connection parts included in the connection part may be the jewel bearing and the top cone. The tip of the top cone is located in the tapered groove of the jewel bearing and is in point contact with the bottom of the tapered groove. When the jewel bearing rotates relative to the top cone, a less frictional force is generated, such that the rotational resistance from the bracket when the supported object rotates can be reduced. The sensitivity and the measurement accuracy of the thrombelastography device may be improved when the bracket is applied to the thrombelastography device.

4. In the embodiment of the present invention, the bracket may comprise at least a pair of magnets, wherein one magnet in each pair of magnets is fixed to the first support part, and the other magnet thereof is fixed to the second support part. The pair of magnets is stacked in parallel, and like magnetic poles are opposite. In this way, according to the principle that like poles repel each other, the magnet on the first support part applies an upward magnetic force to the magnet on the second support part. The magnetic force can reduce the pressure of the point contact between the first connection part and the second connection part, and further reduce the frictional force generated by the point contact, thereby further reducing the rotational resistance encountered when the supported object rotates.

5. In the embodiment of the present invention, the reflective sheet reflects the light emitted by the light emitting module to the light receiving module. When the reflective sheet rotates under the driving of the rotary shaft, since the light emitting module emits light in a fixed direction, the amount of light received by the reflective sheet changes, and at the same time, the optical path of light reflected by the reflective sheet changes due to the rotation of the reflective sheet, resulting in a change in the intensity of light received by the light receiving module that receives the light in the fixed direction. The light receiving module converts the received light into a corresponding electrical signal according to the intensity of the light. The processing module determines the rotation angle of the rotary shaft according to the electrical signal. In this case, the light is taken as a signal for detecting the rotation angle of the rotary shaft. Since the intensity of the light does not change as external factors such as temperature change, the accuracy of detecting the rotation angle of the rotary shaft can be improved by detecting the rotation angle of the rotary shaft through light.

6. In the embodiment of the present invention, the light emitting diode emits light through the light guide column, and the photocell receives light through the light guide column. The light guide column which serves as a light channel can enhance the uniformity of light and prevent the light from being diffusely reflected in the through hole of the fixed light emitting diode or photocell to affect the intensity of the light, thereby ensuring the accuracy of detecting the rotation angle of the rotary shaft.

It should be noted that the terms "processor", "processing unit/module", "controller", "control unit/module" or the like appearing herein may be appropriate devices that are capable of executing appropriate program instructions, arithmetic operations, data processing, and/or control operations and the like. These appropriate devices may be software, hardware, firmware, or a combination thereof, such as, for example, a computer, a central processing unit, or the like. They may be composed of single components or dispersed over a plurality of components according to their functions. They may be a centralized processing system or a distributed processing system.

Aspects of the Invention

The various aspects numbered below further provide the disclosure of the present invention.

1. A bracket, comprising a first support part, a second support part, and a connection part, wherein the first support part supports the second support part by means of the connection part, so that the second support part can rotate relative to the first support part under a first action force;

the first support part comprises: a rotatable structure, a support base, and a stop mechanism, wherein the stop mechanism is used for applying a stop force to the rotation of the rotatable structure;

the rotatable structure is supported on the support base and can rotate relative to the support base under a second action force when the stop force of the stop mechanism is eliminated; and the rotatable structure supports the second support part by means of the connection part, so that the rotatable structure can rotate relative to the second support part while rotating relative to the support base.

2. The bracket according to aspect 1, wherein the rotatable structure comprises a first support member and a bridge structure, wherein the first support member is supported on the support base and can rotate relative to the support base under the second action force when the stop force of the stop mechanism is eliminated;

the bridge structure is supported on the first support member and fixedly connected to the first support member, such that the bridge structure can rotate when the first support member rotates; and the bridge structure supports the second support part by means of the connection part, such that the bridge structure can rotate relative to the second support part when the first support member rotates.

3. The bracket according to aspect 1, wherein the stop mechanism is selected from one of the followings or any combination thereof:

a fixing member for fixing the rotatable structure relative to the support base;

surfaces, which are in contact with each other and have predetermined roughness, of the rotatable structure and the support base; or a material, which provides an eliminable viscous force, between the contact surfaces of the rotatable structure and the support base.

4. The bracket according to aspect 2, wherein the center of the first support member is provided with a first through hole, and the bridge structure is fixed to the first support member across the first through hole;

the center of the support base is provided with a second through hole which is at least partially overlapped with the first through hole;

the center of the second support part is provided with a third through hole; and the second support part passes through the first through hole and the second through hole when being supported by the first support part, and the bridge structure passes through the third through hole and supports the second support part by means of the connection part located in the third through hole.

5. The bracket according to aspect 2, wherein the connection part comprises a first connection part and a second connection part;

the first connection part is fixedly connected to the bridge structure, and the second connection part is fixedly connected to the second support part; and the first connection part and the second connection part are connected together in a form of point contact, such that the first connection part can rotate relative to the second connection part, and further the second support part can rotate relative to the bridge structure.

6. The bracket according to aspect 2, wherein the first support member comprises a support surface and a cylindrical extension part which is located under the support surface and fixedly connected to the support surface; and the top surface, which is in contact with the first support member, of the support base is provided with a groove which is matched with the cylindrical extension part, such that the cylindrical extension part can be accommodated in the groove and supported by the groove, and can rotate in the groove.

7. The bracket according to aspect 2, wherein the first support member comprises a support surface and a cylindrical extension part which is located under the support surface and fixedly connected to the support surface, wherein the support surface extends beyond the upper surface of the cylindrical extension part, such that the support surface protrudes from the side surface of the cylindrical extension part; and the top surface, which is in contact with the first support member, of the support base is provided with a groove which is matched with the cylindrical extension part, such that the cylindrical extension part can be accommodated in the groove, the support surface is supported by the top surface, and further the cylindrical extension art can rotate in the groove.

8. The bracket according to aspect 5, wherein the first connection part is a jewel bearing, and the second connection part is a top cone;

or the first connection part is a top cone, and the second connection part is a jewel bearing; wherein the jewel bearing is provided with a tapered groove, the top cone is of a tapered structure, the tip of the top cone is located in the tapered groove in the jewel bearing, and the top cone is connected to the jewel bearing in a form of point contact.

9. The bracket according to aspect 1, further comprising at least a pair of magnets; wherein for each pair of magnets, the first magnet is fixed to one side, close to the second support part, on the first support part, and the second magnet is fixed to one side, close to the first support part, on the second support part; and the first magnet and the second magnet are stacked in parallel, and two surfaces that are close each other have like magnetic poles.

10. A thrombelastography device, comprising the bracket according to any one of aspects 1 to 9 and a rotary shaft, wherein the lower end of the second support part and one end of the rotary shaft are connected to support the rotary shaft, such that the rotary shaft can rotate under an external driving force.

11. The thrombelastography device according to aspect 10, further comprising a measurement device which is used for measuring a rotation angle of the rotary shaft, and forming a thrombelastogram corresponding to measured blood according to the rotation angle of the rotary shaft.

12. The thrombelastography device according to aspect 11, wherein the measurement device comprises a reflective sheet, a light emitting module, a light receiving module and a processing module; wherein the rotary shaft is fixedly connected to the reflective sheet and drives the reflective sheet to rotate under an external driving force;

the light emitting module is used for emitting light to the reflective sheet in a fixed direction;

the reflective sheet is used for receiving light emitted by the light emitting module and reflecting the received light;

the light receiving module is used for receiving light reflected by the reflective sheet in a fixed direction, converting the received light into a corresponding electrical signal according to the intensity of the light, and transmitting the electrical signal to the processing module; and the processing module is used for processing the electrical signal converted by the light receiving module to determine the rotation angle of the rotary shaft.

13. The thrombelastography device according to aspect 12, wherein the light emitting module comprises a light emitting diode and a light guide column, wherein the light emitting diode emits light to the reflective sheet through the light guide column;

and/or the light receiving module comprises a photocell and a light guide column, wherein the photocell receives light reflected by the reflective sheet through the light guide column.

14. A support system, comprising the bracket according to any one of aspects 1 to 9, and a supported object, wherein the lower end of the second support part and one end of the supported object are connected to support the supported object, such that the supported object can rotate under an external driving force.

15. A use method for the thrombelastography device according to any one of aspects 10 to 13, comprising:

eliminating a stop force of the stop mechanism in response to the first support part being offset from the second support part by a predetermined position;

rotating the first support member by applying the second action force to the first support member, such that the bridge structure rotates relative to the second support part to a position that forms a predetermined angle with the second support part;

inserting the lower end of the rotary shaft to measured blood;

rotating the measured blood to drive the rotary shaft to rotate; and calculating blood coagulation data of the measured blood based on the measured rotation angle of the rotary shaft.

It should be eventually noted that the above contents are only preferred embodiments of the present invention, and used only for describing the technical solutions of the present invention, rather than limiting the protection scope of the present invention. Any modifications, equivalents, improvements, etc. made within the spirit and principle of the present invention should be included within the protection scope of the present invention.

The invention claimed is:

1. A bracket, comprising: a first support part, a second support part, and a connection part, wherein
the first support part supports the second support part by means of the connection part, so that the second support part can rotate relative to the first support part under a first action force;
the first support part comprises:
a rotatable structure, a support base, and a stop mechanism, wherein
the stop mechanism is used for applying a stop force to the rotation of the rotatable structure, wherein
the rotatable structure is supported on the support base and can rotate relative to the support base under a second action force when the stop force of the stop mechanism is eliminated,
the rotatable structure comprises a first support member and a bridge structure, wherein
the first support member is supported on the support base and can rotate relative to the support base under the second action force when the stop force of the stop mechanism is eliminated,
the bridge structure is supported on the first support member and fixedly connected to the first support member, such that the bridge structure rotates when the first support member rotates; and
the bridge structure supports the second support part by means of the connection part, such that the bridge structure rotates relative to the second support part when the first support member rotates, and
the rotatable structure supports the second support part by means of the connection part, so that the rotatable structure can rotate relative to the second support part while rotating relative to the support base;
wherein the center of the first support member is provided with a first through-hole, and the bridge structure is fixed to the first support member across the first through-hole;

the center of the support base is provided with a second through-hole which is at least partially overlapped with the first through-hole;
the center of the second support part is provided with a third through-hole; and
the second support part passes through the first through-hole and the second through-hole when being supported by the first support part, and the bridge structure passes through the third through-hole and supports the second support part by means of the connection part located in the third through-hole.

2. The bracket according to claim 1, wherein the stop mechanism is selected from one of the followings or any combination thereof:
a fixing member for fixing the rotatable structure relative to the support base;
surfaces, which are in contact with each other and have predetermined roughness, of the rotatable structure and the support base; or
a material, which provides an eliminable viscous force, between the contact surfaces of the rotatable structure and the support base.

3. The bracket according to claim 1, wherein
the connection part comprises a first connection part and a second connection part;
the first connection part is fixedly connected to the bridge structure, and the second connection part is fixedly connected to the second support part; and
the first connection part and the second connection part are connected together in a form of point contact, such that the first connection part can rotate relative to the second connection part, and further the second support part can rotate relative to the bridge structure.

4. The bracket according to claim 3, wherein
the first connection part is a jewel bearing, and the second connection part is a top cone;
or
the first connection part is a top cone, and the second connection part is a jewel bearing; wherein
the jewel bearing is provided with a tapered groove, the top cone is of a tapered structure, the tip of the top cone is located in the tapered groove in the jewel bearing, and the top cone is connected to the jewel bearing in a form of point contact.

5. The bracket according to claim 1, wherein
the first support member comprises a support surface and a cylindrical extension part which is located under the support surface and fixedly connected to the support surface; and
the top surface, which is in contact with the first support member, of the support base is provided with a groove which is matched with the cylindrical extension part, such that the cylindrical extension part can be accommodated in the groove and supported by the groove, and can rotate in the groove.

6. The bracket according to claim 1, wherein
the first support member comprises a support surface and a cylindrical extension part which is located under the support surface and fixedly connected to the support surface, wherein the support surface extends beyond an upper surface of the cylindrical extension part, such that the support surface protrudes from the side surface of the cylindrical extension part; and
wherein the support part comprises a top surface, which is in contact with the first support member, and is provided with a groove which is matched with the cylindrical extension part, such that the cylindrical extension part can be accommodated in the groove, the support surface is supported by the top surface, and further the cylindrical extension part can rotate in the groove.

7. The bracket according to claim 1, further comprising at least a pair of magnets; wherein for each pair of magnets, the first magnet is fixed to one side, close to the second support part, on the first support part, and the second magnet is fixed to one side, close to the first support part, on the second support part; and the first magnet and the second magnet are stacked in parallel, and two surfaces that are close each other have like magnetic poles.

8. A thrombelastography device, comprising the bracket according to claim 1 and a rotary shaft, wherein the lower end of the second support part and one end of the rotary shaft are connected to support the rotary shaft, such that the rotary shaft can rotate under an external driving force.

9. The thrombelastography device according to claim 8, further comprising a measurement device which is used for measuring a rotation angle of the rotary shaft, and forming a thrombelastogram corresponding to measured blood according to the rotation angle of the rotary shaft.

10. The thrombelastography device according to claim 9, wherein
the measurement device comprises a reflective sheet, a light emitting module, a light receiving module and a processing module; wherein
the rotary shaft is fixedly connected to the reflective sheet and drives the reflective sheet to rotate under an external driving force;
the light emitting module is used for emitting light to the reflective sheet in a fixed direction;
the reflective sheet is used for receiving light emitted by the light emitting module and reflecting the received light;
the light receiving module is used for receiving light reflected by the reflective sheet in a fixed direction, converting the received light into a corresponding electrical signal according to the intensity of the light, and transmitting the electrical signal to the processing module; and
the processing module is used for processing the electrical signal converted by the light receiving module to determine the rotation angle of the rotary shaft.

11. The thrombelastography device according to claim 10, wherein
the light emitting module comprises a light guide column and at least one of:
a light emitting diode, wherein the light emitting diode emits light to the reflective sheet through the light guide column; or
a photocell, wherein the photocell receives light reflected by the reflective sheet through the light guide column.

12. A use method for the thrombelastography device according to claim 8, comprising:
eliminating a stop force of the stop mechanism in response to the first support part being offset from the second support part by a predetermined position;
rotating the first support member by applying the second action force to the first support member, such that the bridge structure rotates relative to the second support part to a position that forms a predetermined angle with the second support part;
inserting the lower end of the rotary shaft to measured blood;
rotating the measured blood to drive the rotary shaft to rotate; and
calculating blood coagulation data of the measured blood based on the measured rotation angle of the rotary shaft.

13. A support system, comprising the bracket according to claim 1, and a supported object, wherein the lower end of the second support part and one end of the supported object are connected to support the supported object, such that the supported object can rotate under an external driving force.

14. The support system of claim 13, wherein the stop mechanism is selected from one of the followings or any combination thereof:
a fixing member for fixing the rotatable structure relative to the support base;
surfaces, which are in contact with each other and have predetermined roughness, of the rotatable structure and the support base; or
a material, which provides an eliminable viscous force, between the contact surfaces of the rotatable structure and the support base.

15. The support system of claim 13, wherein
the connection part comprises a first connection part and a second connection part;
the first connection part is fixedly connected to the bridge structure, and the second connection part is fixedly connected to the second support part; and
the first connection part and the second connection part are connected together in a form of point contact, such that the first connection part can rotate relative to the second connection part, and further the second support part can rotate relative to the bridge structure.

16. The support system of claim 13, wherein
the first support member comprises a support surface and a cylindrical extension part which is located under the support surface and fixedly connected to the support surface, wherein the support surface extends beyond an upper surface of the cylindrical extension part, such that the support surface protrudes from the side surface of the cylindrical extension part; and
wherein the support base comprises a top surface, which is in contact with the first support member, and is provided with a groove which is matched with the cylindrical extension part, such that the cylindrical extension part can be accommodated in the groove, the support surface is supported by the top surface, and further the cylindrical extension part can rotate in the groove.

17. The support system of claim 13, wherein the bracket further comprises at least a pair of magnets; wherein
for each pair of magnets, the first magnet is fixed to one side, close to the second support part, on the first support part, and the second magnet is fixed to one side, close to the first support part, on the second support part; and
the first magnet and the second magnet are stacked in parallel, and two surfaces that are close each other have like magnetic poles.

18. The bracket according to claim 1, wherein
the first support member comprises a support surface and a cylindrical extension part which is located under the support surface and fixedly connected to the support surface; and
the top surface, which is in contact with the first support member, of the support base is provided with a groove which is matched with the cylindrical extension part, such that the cylindrical extension part can be accommodated in the groove and supported by the groove, and can rotate in the groove.

* * * * *